United States Patent
Mickle et al.

(10) Patent No.: US 6,289,237 B1
(45) Date of Patent: Sep. 11, 2001

(54) APPARATUS FOR ENERGIZING A REMOTE STATION AND RELATED METHOD

(75) Inventors: Marlin H. Mickle, Pittsburgh; Kevin W. Wells, Harmony; Ronald G. Hoelzeman, Pittsburgh, all of PA (US)

(73) Assignee: University of Pittsburgh of the Commonwealth System of Higher Education, Pittsburgh, PA (US)

(*) Notice: Subject to any disclaimer, the term of this patent is extended or adjusted under 35 U.S.C. 154(b) by 0 days.

(21) Appl. No.: 09/218,322

(22) Filed: Dec. 22, 1998

(51) Int. Cl.[7] .................................................. A61B 5/402
(52) U.S. Cl. ........................................ 600/509; 128/903
(58) Field of Search ................................ 607/33, 31, 32, 607/61; 128/903; 600/300, 308

(56) References Cited

U.S. PATENT DOCUMENTS

| | | |
|---|---|---|
| 4,129,125 | 12/1978 | Lester et al. . |
| 4,166,470 * | 9/1979 | Neumann .............................. 607/33 |
| 4,308,870 | 1/1982 | Arkans . |
| 4,356,825 | 11/1982 | Veth . |
| 4,432,363 * | 2/1984 | Kakegawa .............................. 607/33 |
| 4,443,730 | 4/1984 | Kitamura et al. . |
| 4,494,553 | 1/1985 | Sciarra et al. . |
| 4,576,179 | 3/1986 | Manus et al. . |
| 4,889,131 | 12/1989 | Salem et al. . |
| 5,230,342 | 7/1993 | Bobo, Jr. et al. . |
| 5,335,551 | 8/1994 | Ohnishi et al. . |
| 5,387,259 * | 2/1995 | Davidson ............................. 600/300 |
| 5,586,555 | 12/1996 | Bobo, Jr. et al. . |
| 5,729,572 | 3/1998 | Oh . |
| 5,736,937 | 4/1998 | McGirr et al. . |
| 5,760,558 | 6/1998 | Popat . |
| 5,768,696 | 6/1998 | Law . |
| 5,808,760 | 9/1998 | Gfeller . |
| 5,815,807 | 9/1998 | Osmani et al. . |
| 5,841,122 | 11/1998 | Kirchhoff . |
| 5,844,516 | 12/1998 | Viljanen . |
| 5,862,803 | 1/1999 | Besson et al. . |
| 5,874,723 | 2/1999 | Hasegawa et al. . |

\* cited by examiner

*Primary Examiner*—Jeffrey R. Jastrzab
(74) *Attorney, Agent, or Firm*—Arnold B. Silverman; Eckert Seamans Cherin & Mellott, LLC (57) ABSTRACT

Apparatus for remote interaction with an object of interest includes a remote station for obtaining information from the object of interest, a base station for transmitting energy in space to and communicating with the remote station and the remote station having a conversion device for energizing the remote station responsive to receipt of the transmitted energy. The energy may be of any suitable type including RF power, light, acoustic, magnetic energy or other form of space transmitted or "radiant" energy. The remote station does not have to contain a source of stored energy or a wired connection to a source of energy. The remote station receives the energy transmission and data transmission from the base station and transmits data to the base station. Microprocessor controllers may be provided for the base station and the remote station. The remote station may receive information from sensors and through one or more transponders sequentially communicate information to the base station. An associated method is provided.

40 Claims, 5 Drawing Sheets

APPARATUS FOR ENERGIZING A REMOTE STATION AND RELATED METHOD

BACKGROUND OF THE INVENTION

1. Field of the Invention

This invention relates to apparatus and an associated method for energizing a remote station through energy transmitted in space and, more specifically, it relates to such a system wherein data with respect to an object of interest may be obtained by the remote station and transmitted to the base station upon interrogation by the base station.

2. Description of the Prior Art

It has long been known in various applications to monitor conditions of a physical system or a patient and provide information in the nature of real-time readouts of certain conditions. Such systems typically have been connected by a suitable wire to a source of electricity at the desired voltage such as line current or batteries.

It has also been known to provide such systems in the medical environment in respect of monitoring characteristics such as patient respiration, heart beat, electrocardiograms and temperature, for example. See, generally, U.S. Pat. Nos. 4,129,125; 4,308,870; 4,443,730; 4,889,131; and 5,335,551.

It has also been known in the medical environment to monitor physiological parameters by employing sensors, a battery powered system, and digital processing means to effect comparison between the measured conditions and stored values and displaying the results. See U.S. Pat. No. 4,356,825.

U.S. Pat. Nos. 5,230,342 and 5,586,555 disclose blood pressure monitors employing a pressurizable pressure transducing bladder with particular emphasis on measuring blood pressure in a supraorbital artery.

U.S. Pat. No. 4,576,179 discloses the use of a chest motion transducer and associated heart rate monitoring apparatus. Cooperating electronics are provided. Alarm means may be triggered under appropriate conditions of the individual being monitored or an indication that the battery voltage has fallen below a preset level. There is an allusion to making provision for short range radio transmission of the signals to remote monitoring stations. See also U.S. Pat. No. 5,022,402.

U.S. Pat. No. 4,494,553 discloses a battery powered respiratory and cardiac monitor wherein a pair of inductance coils are employed along with VHF/FM transmission of signals.

In spite of the foregoing known systems, there remains a need for a remote unit usable in various environments and at various distances from the base station which remote unit will be adapted to be remotely energized so as not to require hard wired systems or batteries on the remote unit. There is also lacking such systems wherein the remote unit may be miniaturized so as to have numerous potential uses.

SUMMARY OF THE INVENTION

The present invention has met the above-described needs. In the present invention, apparatus for remote interaction with an object of interest includes a remote station for obtaining information from the object of interest and a base station for transmitting energy in space to the remote station and communicating with the remote station. The remote station has conversion means for energizing the remote station by employing the transmitted energy. The base station may transmit the energy as RF power, light, acoustic, magnetic, or in other suitable forms of space transmitted or "radiant" energy.

A power supply is provided for energizing the base station with first antenna means being provided on the base station and second antenna means being provided on the remote station. Sensor means or other information providing means permits the remote station when energized by the base station to transmit information to the base station regarding the object of interest and certain conditions of the remote station. This may be done in real-time. The remote station may be provided with a plurality of transponders each of which may be interrogated by the base station sequentially to provide separate informational packets.

A method of the present invention provides for remote interaction with an object of interest, including providing the remote station and a base station operatively associated therewith, with energy being transmitted in space from the base station to the remote station, and the energy so transmitted being converted by the remote station into electrical power to energize the remote station.

The remote station may be provided with a plurality of transponders each of which will be a source of different information from the other.

The system eliminates the need for batteries on the remote station or the use of hard wired systems.

It is object of the present invention to provide a remote station which is adapted to provide information to a base station when interrogation by the base station is initiated.

It is another object of the present invention to provide such a system wherein the remote station is not required to contain an energy storage device, such as a battery, or to be part of a hard wired or printed circuit system.

It is a further object of the present invention to provide such a system wherein energy transmitted in space, such as RF power or light, will be converted into DC power or AC power on the remote station to operate the remote station.

It is a further object of the present invention to provide such a system wherein RF power may be employed to initiate operation of the remote station regardless of whether light is present.

It is a further object of the present invention to provide such a remote station which will transmit dynamic real-time measurements to a base station.

It is another object of the present invention to provide such a system wherein the remote station may be miniaturized and does not require frequent maintenance.

It is a further object of the present invention to provide such a system wherein the remote station may have a plurality of passive intelligent transponders.

These and other objects of the invention will be more fully understood from the following description of the invention on reference to the accompanying drawings.

DESCRIPTION OF THE PREFERRED EMBODIMENTS

As employed herein, the term "object of interest" means any animate or inanimate item from which information is to be obtained by the remote station.

As employed herein, the term "in space" means that energy or signals are being transmitted through the air or similar medium regardless of whether the transmission is within or partially within an enclosure, as contrasted with transmission of electrical energy by a hard wired or printed circuit boards.

As employed herein, the term "patient" means members of the animal kingdom including humans.

Figure 1:
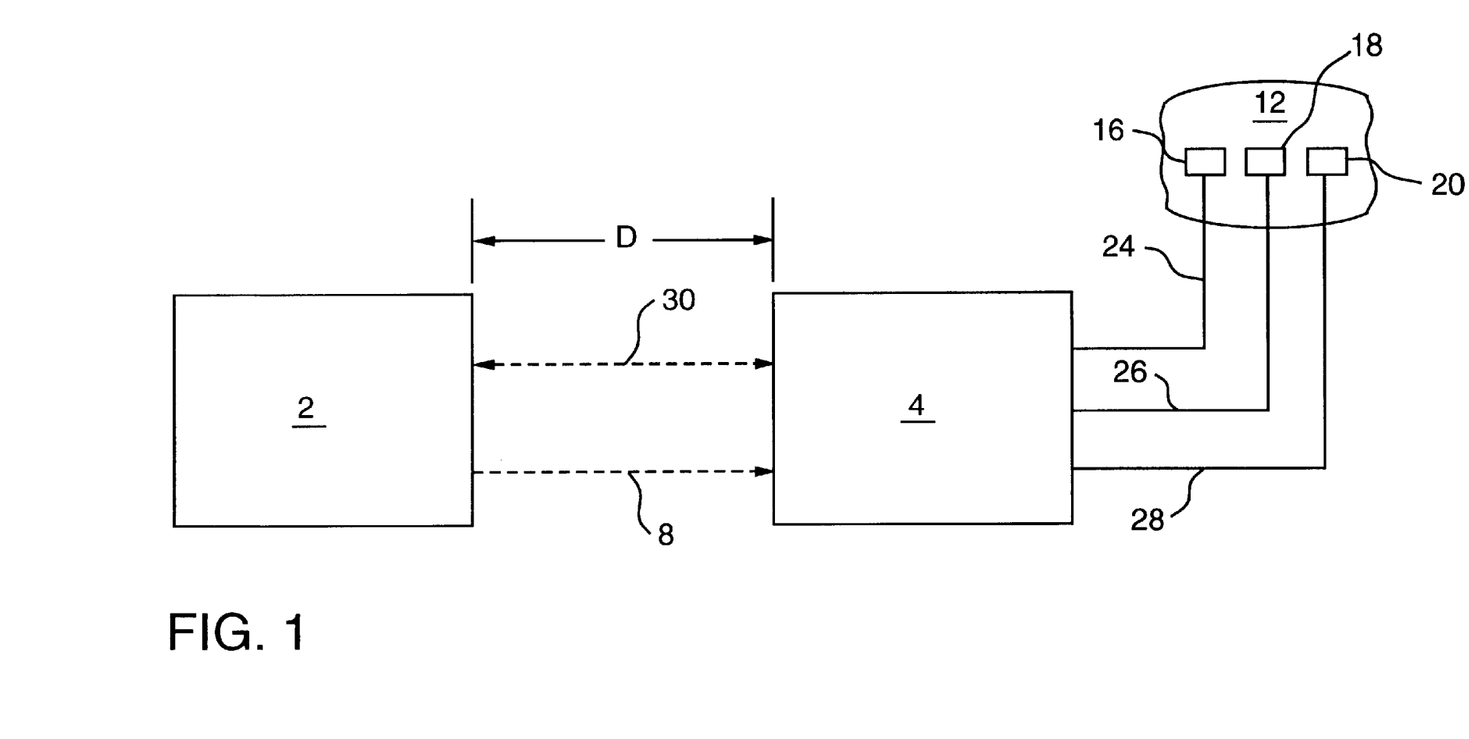
FIG. 1 is a schematic illustration of a form of the present invention showing a base station, a remote station, and a plurality of information providing sensors.

Referring to FIG. 1, there is shown a schematic illustration of the apparatus of the present invention which facilitates remote measurement and/or sensing. A base station 2 is within communication distance D of a remote station 4. In a manner to be described hereinafter, the base station 2 transmits energy which may be RF power, light, acoustic, magnetic or other suitable forms of space transmitted or "radiant" energy, for example, and is indicated generally by the dashed line 8 to remote station 4. Within the remote station 4, the received energy is converted into DC power which serves to operate the remote station 4. In the form illustrated, an object of interest 12 has a plurality of sensors 16, 18, 20 operatively associated therewith, and delivering sensor readings over lines 24, 26, 28, respectively, to the remote station 4 which, in turn, in a manner to be described herein, transmits data through space as indicated by double-headed arrow 30 to base station 2. The power delivered to remote station 4 may also energize sensors 16, 18, 20 through wires 24, 26, 28. The RF energy may also be employed to energize sensors 16, 18, 20 without wires 24, 26, 28. The distance D will vary in accordance with design parameters of the system and may, depending upon the application, be a few millimeters, several feet, or several light years. Dashed arrow 30 also shows data being transmitted from base station 2 to remote station 4.

One of the advantages of the present invention is that the source of power for the remote station 4 is the base station 2 and, therefore, there is no need for hard wiring or printed circuit physical connections with remote station 4. There is also no need for remote station 4 to carry an electrical storage device such as a battery. As a result, activation and powering of the remote station 4 will be achieved through activation of the base station 2. As a result, there will be no need for periodic maintenance on the remote station 4 in order to check battery strength and replace the battery or other power source. This also facilitates the remote station being encapsulated within a suitable protective material, such as a resinous plastic. Homopolymers (including thermoplastic polymers), elastomers and silicon dioxide, for example, are suitable materials for such purposes. Further, this facilitates miniaturization of the remote station and placing the remote station in functionally desirable locations which need not be readily accessible. The remote station, for example, could be implanted in a patient.

It will be appreciated that the remote station 4 can be interrogated by the base station 2, for example, to provide through the remote station 4 a reading of an electronic or mechanical sensor, such as 16, 18, 20 which is operatively associated with the remote station 4.

Figure 2:
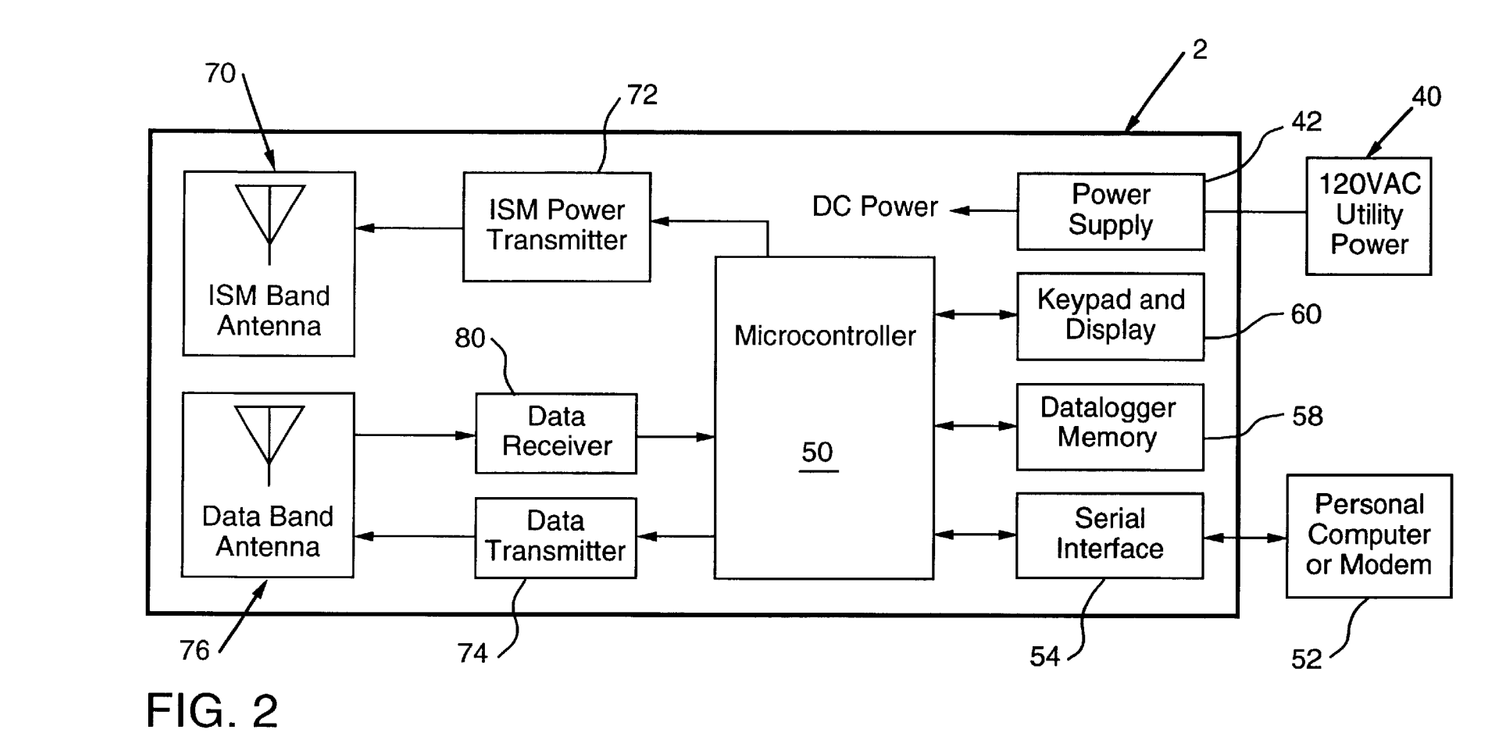
FIG. 2 is a schematic illustration of a base station usable in the present invention.

Referring to FIG. 2 in greater detail, there is shown a schematic diagram of a form of base station 2 usable in the present invention. The base station 2 is, in the form shown, energized by a 120 VAC utility power source 40, although other power sources, such as batteries, alternators and inverters, for example, may be employed, if desired. The power source is in communication with and supplies power to power supply 42 which, in turn, emits DC power at the desired level for operation of the base station 2. If desired, AC power could be employed to energize the remote station 4. A microcontroller 50, which may take the form of a microprocessor or intelligent microchip, which receives input from an analog to digital converter, a transducer employing an electronic means (such as sound, light, temperature, moisture or the like) or a program in memory, hard wired logic, an Application Specific Integrated Circuit (ASCI), from a wireless link, a satellite or cable, as in TV, for example.

A computer 52, which may be any sort of personal computer or modem if the unit is on a network, through serial interface 54 provides two-way communication with microcontroller 50. The datalogger memory 58 is in two-way communication with the microcontroller 50 and functions to provide the microcontroller 50 with any desired comparison standards, basic data, and calibration information. The keypad and display 60 is in two-way communication with microcontroller 50 and provides for keypad input into the microcontroller 50 and display of information obtained by the base station 2.

The base station 2 has an ISM (Industrial, Scientific, Medical) band antenna 70 which transmits RF signals emitted by the ISM power transmitter 72 responsive to signals received from microcontroller 50.

This serves to transmit the RF power in space to the remote station 4. In the event that light were to be the transmitted energy. The transmitted energy source may be the sun, room light, (incandescent or fluorescent) or laser light, for example. This one-way transmission is shown by the dashed arrow line 8 in FIG. 1.

The base station 2 has data transmitter 74 which has data transmitted by data band antenna 76 to the remote station 4. The data transmitted may be control, configuration, identification and processed versions of such data.

Microcontroller 50 controls data transmitter 74. Data receiver 80 receives data from the remote station 4 through data band antenna 76 and introduces the same into microcontroller 50.

It will be appreciated that in this manner the power supplied to the base station 2 not only serves to operate the base station 2, but provides the means for transmitting energy in space to remote station 4 to operate the same and transmit data to and receive data from remote station 4.

Figure 3:
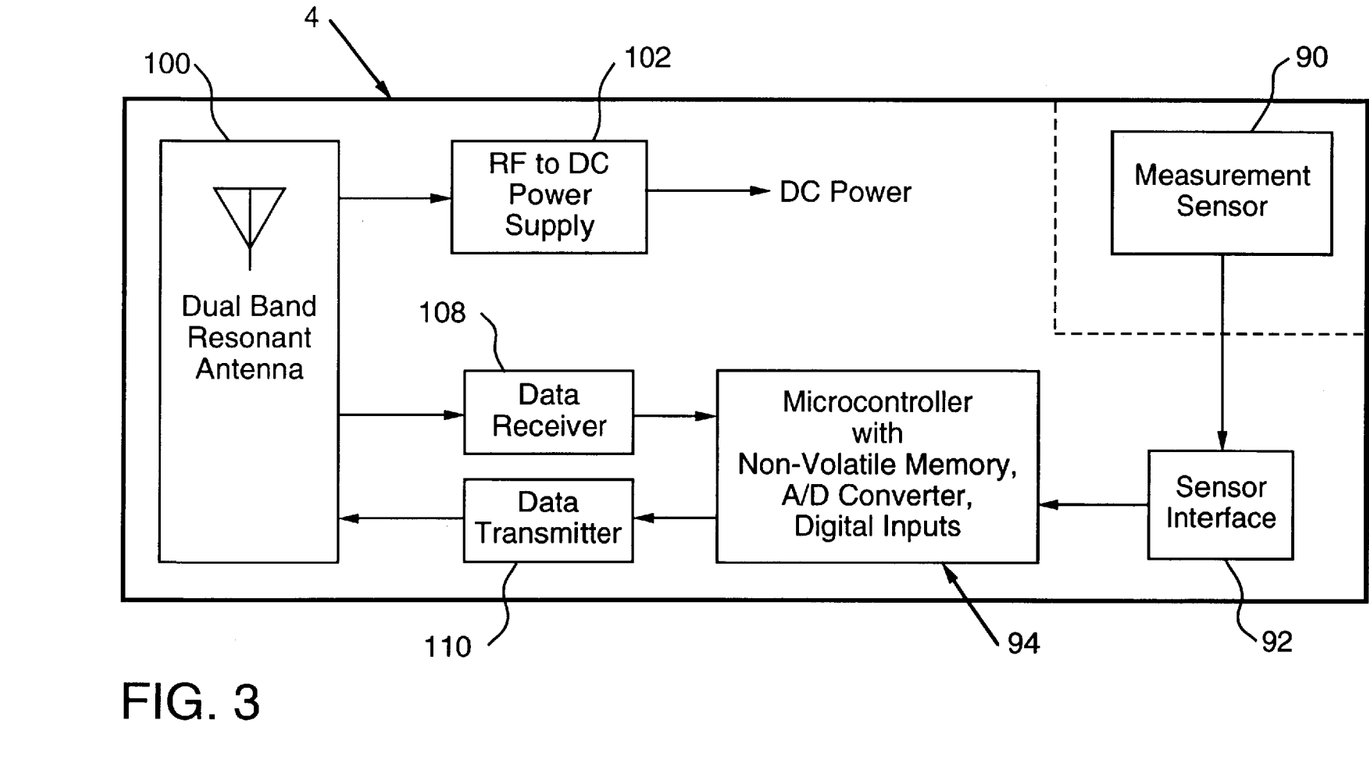
FIG. 3 is a schematic illustration of a remote station and associated sensor usable in the present invention.

Referring to FIG. 3 in greater detail, there is shown a form of remote station 4 which, in the form shown, cooperates with a measurement sensor 90 which senses an object of interest, through a sensor interface 92, interacts with microcontroller 94 which preferably has a non-volatile memory and through an analog to digital converter, direct digital measurement device or other sampling device, provides for digital input into the microcontroller 94. This microcontroller 94 controls operation of the remote station 4. A dual band resonant antenna 100 receives both the power transmissions and data transmissions from the base station 2. The power transmission is received in the converter 102, which converts the RF power to DC power, which serves to energize the remote station 4. In the alternative, a device for converting the RF power into AC power could be employed to power the remote station 4. This substitutes for the need to provide a hard wired system or to have a power storage device on the remote station. The data received from the base station 2 is delivered by the antenna 100 to data receiver 108 which, in turn, delivers the same to the microcontroller 94. This data initiates a cycle of operation of the remote station 4 and serves as the interrogation means. The data could also be data for controlling other functions such as ON/OFF switching, calibration, remote control or configuration control.

Data processed by the microcontroller 94 and received in the form shown from measurement sensor 90 is transmitted by data transmitter 110 through a double band resonant antenna 100 to base station 2 as indicated by the double-headed dashed arrow 30 in FIG. 1. It will be appreciated, therefore, that positioning of the remote station 4 with respect to the base station 2 will be heavily dependent on the application intended and will involve design of the system to provide adequate RF power and sufficient antenna capability to maintain the desired level of power for the remote station 4 and efficient communication of data between the remote station 4 and base station 2.

Numerous end use applications will be apparent to those skilled in the art. For example, in many applications the distance D in FIG. 1 will be less than 20 feet. In medical applications such as, for example, where the sensors 16, 18, 20 might be EKG sensors, a plurality of remote stations each having a sensor built into it or operatively associated therewith may be applied to the object of interest 12 which, in that case, would be a patient, such that no wires need be provided. In the alternative, in the form shown in FIG. 1, no wires need to be provided between the remote station 4 and the base station 2. Many other types of medical applications wherein sensors or information gathering apparatus is employed, such as cardiac monitors, brain monitors, pulse monitors, blood pressure monitors, oxygen monitors, as well as monitors which monitor the performance of patient support equipment, such as ventilators, intravenous delivery systems, renal dialysis machines, oxygen supplementing devices and heart bypass devices may beneficially employ the invention. Depending upon the end use, it might also be desirable to have an alarm triggered in addition to the visual presentation or computer storage or hard copy presentation of information obtained from the system.

In an alternate embodiment of the invention, uses in manufacturing processes so as to monitor equipment performance or product manufacture may advantageously find uses for the present invention. The system may also be employed for noise monitoring of equipment and providing communication for Computer Numeric Control (CNC), for example.

In some instances, where identification is desired, such as for security purposes, the remote unit might provide information to enable the base unit to confirm that an article or an individual is as represented.

In retail stores, products may have remote stations of the present invention secured thereto which at the cash register will deliver information to a base station thereby eliminating the need for bar codes and the like. This could be employed to total the charges for a specific customer as well inventory control and keep records of customer preferences.

There also may be applications involving outer space wherein the remote station provides information to an earth mounted base station.

Other uses will be apparent to those skilled in the art. A key feature is that the present system obviates the need to depend on batteries and hard wired systems as a source of energizing a remote station. Both power delivery to the remote station and two-way data transmission between the base station and the remote station are facilitated.

Figure 4:
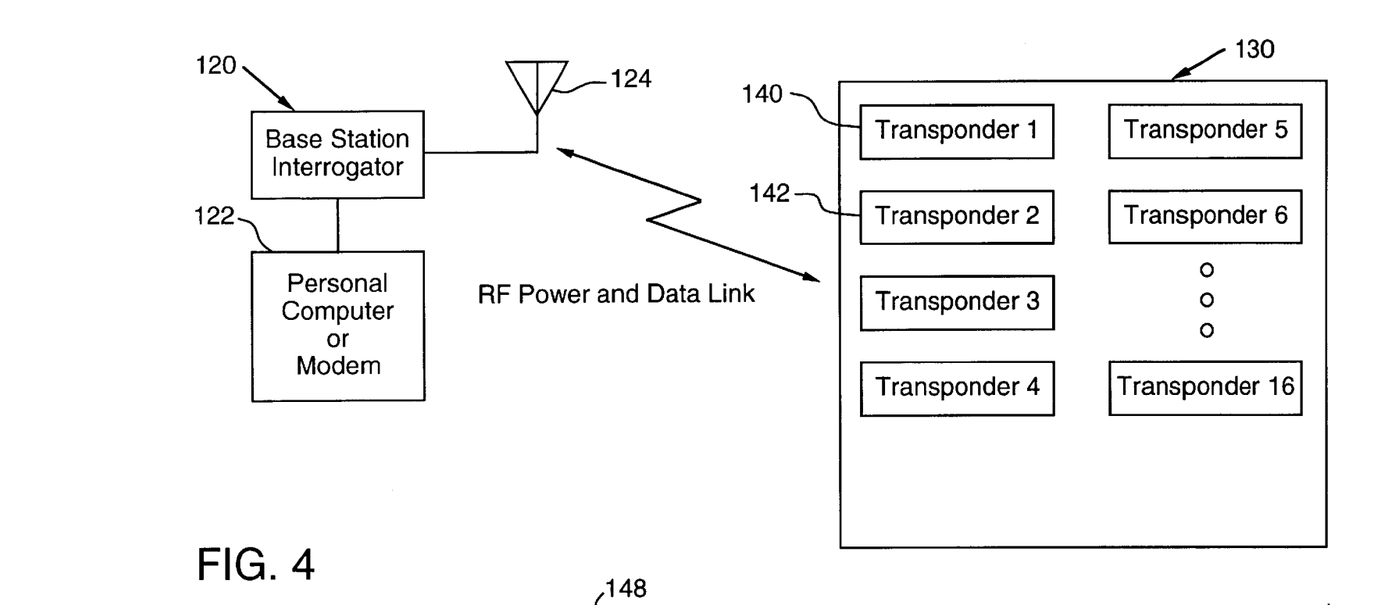
FIG. 4 is a schematic illustration of an embodiment of the present invention employing a plurality of transponders in the remote station.

Referring to FIG. 4, there is shown a system wherein the base station 120 and its associated microprocessor 122, which may be a personal computer or modem, cooperates with antenna 124 to provide for power delivery and two-way data communication with the remote station 130. As shown in FIG. 4, this embodiment contemplates the use of a plurality of transponders, such as 140, 142 which, in the form shown, total 16 in number. It is contemplated in this embodiment that each transponder will be operatively associated with a sensor receiving one type of information and will facilitate the base station sequentially interrogating each transponder 140, 142 to receive real-time information therefrom with a suitable time interval between each interrogation. Depending on the application, in lieu of sensor information, the interrogation may be to determine product codes or personal identification of an individual.

Figure 5:
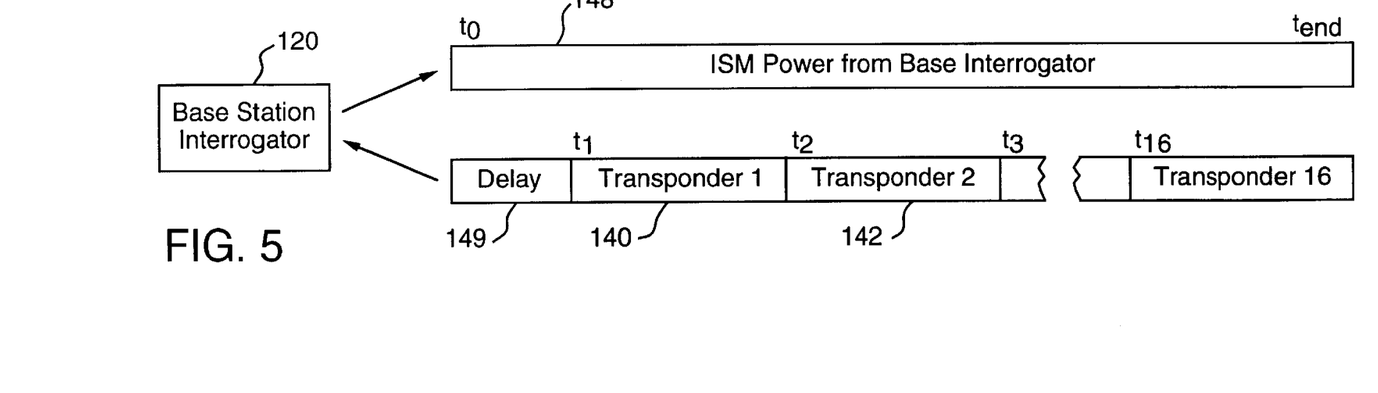
FIG. 5 is a schematic illustration of the base station interrogator and the corresponding time sequence of interrogating a plurality of transponders.

Referring to FIG. 5 there is shown a suitable communications protocol for use in the system of the present invention. The base station 120 provides means for identifying the specific transponder which is the source of the data being received and does so by polling each transponder in sequence. The power signal sent by the base station 120 may be employed as a means of providing a signal to identify the start of the polling operation. Depending upon the system address of the transponder, the data sent back will be sent at a unique time. The ISM power interrogator 148 after an initial delay period indicated generally by the reference number 149, each transponder such as transponder 140 which will be interrogated between times $t_1$ and $t_2$ and transponder 142 will be interrogated between times $t_2$ and $t_3$. In this manner, the discrete data packets received from the various transponders will be provided sequentially with identification as to source. It is preferred that a short dead time be provided between successive transponder data packets in order to avoid collisions. The data packets from the transponder may contain both sensor data and status information. The sensor data will be the information provided from the sensor through the system described hereinbefore. The status information may include information such as the specific transponder address identification, the internal DC bus voltage and, if desired, discrete digital inputs. The base interrogator will use the status information to verify the integrity of the communication links and have the capability of altering the ISM power if necessary.

Figure 6:
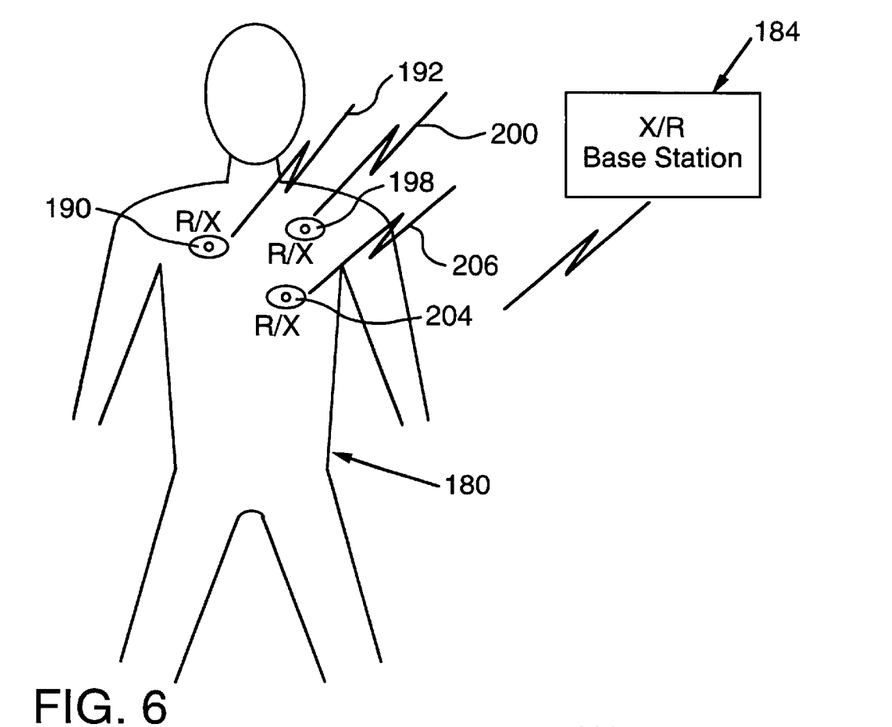
FIG. 6 is a schematic view of a plurality of electrocardiogram sensors and associated transponders, as well as the base station, which is in space communication therewith.

Referring to FIG. 6, there is shown the outline of a patient 180 with a plurality of sensors and associated remote stations 190, 198, 204, with a symbolic representation of the space communications as by RF signals 192, 200, 206 with the base station 184. In the R/X and X/R representations, the "R" indicates receiving capability and the "X" indicates transmitting capability.

Figure 7:
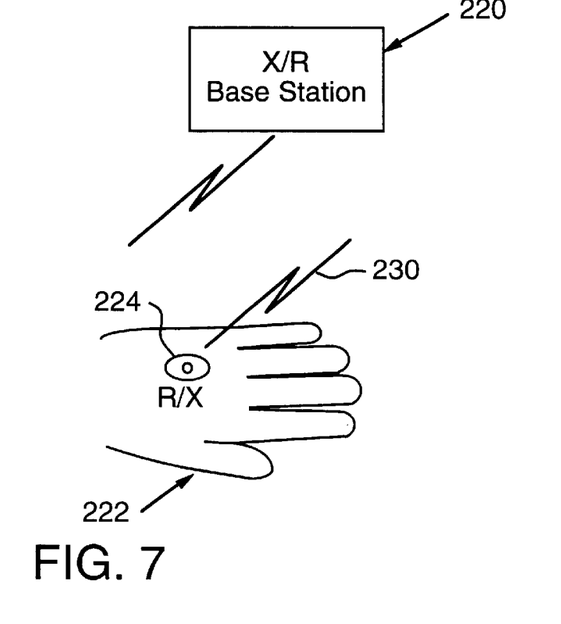
FIG. 7 is a schematic illustration of a base station in space communication with a sensor and remote station combination secured to an individual's hand to provide monitoring of the patient.

Referring to FIG. 7, there is shown a schematic of a base station 220 in space contact as by transmission of RF power shown schematically at 230 to hand 222 which contains a sensor for medical information such as pulse, blood pressure or temperature, for example, operatively associated with the remote station 224.

EXAMPLE

In order to provide additional insight into the invention an example will be provided.

A system of the type discussed in connection with FIGS. 1–3 may have a base interrogator unit or base station powered by standard commercial 120 VAC utility or equivalent UPS. If the ISM power is limited to 16 watts, then the total input power need not exceed 20 watts. The ISM power transmitter 72 will preferably be capable of outputting less than 1 watt or 1, 2, 4, 8, or 16 watts of RF energy as determined by the microcontroller 50. This will facilitate flexibility in respect of power for the program instructions and set-up parameters. An asynchronous serial port serves to connect the base station to the personal computer or modem 52 by way of an RS232 type interface. A suitable microcontroller 50 would be that marketed under the trade designation "Intel 8051." The keypad and display 60 permits users to monitor measurement data and status from the system's transponders. The keypad switches allow the user to step through a menu driven display at various parameters. The keypad may also have a password function to provide for security for restricted set up of the system parameters.

The datalogger memory 58 permits the base station to have the capability to pole multiple transponder devices in a typical system configuration. A non-volatile memory facilitates logging time stamped transponder data in a file storage buffer which can be used for data trending and uploaded by way of the serial interface 54. The non-volatile memory can be interfaced directly to the microcontroller bus as SRAM module with a real-time clock. The serial interface 54 allows connection either to a personal computer or modem. Software, firmware, ASCI or wired logic resident in the base station may include drivers for an ASCII station communication protocol in order that the system can be configured by way of a PC GUI menu system. The modem drivers will allow the base station to stand alone and accept, as well as generate telephone communications. The system firmware, non-volatile parameters and datalogger memory are all accessible by way of the serial interface 54. The power supply 42 serves to convert the 120 VAC utility input to low voltage DC to operate the control circuitry and RF transmitter. The power supply should output a well regulated 5 VDC (±15%) for the logic circuits and a 12–24 VDC output to operate the ISM power transmitter 72.

The remote station, as shown in FIG. 3, can be miniaturized and preferably has maximum dimensions of about 5 inches by 2 inches by 1 inch. The size may be reduced to the point where the remote station may implanted into the human body. One limiting factor in miniaturization is the antenna and as a result, it is preferred to raise the operating frequency as high as practical. The transponders may be about 0.5 inch in diameter and have a thickness of about 0.03215 inch.

The remote station contains no power storage device as all power is derived from the base station. Experimental results have indicated that at least 20 mw of usable DC power can be obtained in the remote station through the system described herein. The transponder has a direct-coupled analog input for interfacing with the measurement sensors. The analog to digital converter may have an input range of 0–2.5 VDC. The ISM E-field at the remote station may be approximately 3 V/m with the specific field depending upon the effective antenna gain. With respect to the telemetry link, data is returned by way of a communication link that operates outside the ISM band. The base station data receiver may have a sensitivity on the order of 0.5 uv/m. The remote station datalink RF output will generally be less than 10 mw which facilitates reliable communications over the required range. The converter serves to transform the ISM RF power into DC bus voltage on the order of 3 VDC. The RF energy coupled into the remote station antenna is an AC voltage varying at the carrier frequency. The RF to DC converter circuit rectifies and filters the RF AC voltage into a usable DC form. The rectifier and filter circuit preferably has an impedance several times lower than the overall antenna with the antenna having a characteristic impedance on the order of 377 ohms and the rectifier circuit having an impedance less than 10 ohms. A suitable microcontroller for use in the remote station is that sold under the trade designation Microchip PIC.

It will be appreciated, therefore, that the present invention provides an effective means for establishing a system wherein a base station cooperates with a remote station by exchanging data in both directions with the base station serving to provide transmitted energy which serves to energize the remote station to permit functioning thereof. As a result, there is no need to have a wired system connecting the remote station with a source of power or for it to carry a power storage unit. This permits low or no maintenance remote systems which may be implanted in individuals, used for other medical purposes, used in space, industry, security and a wide range of other uses. All of this is accomplished in a simple, efficient manner employing the apparatus and methods of the present invention.

While for simplicity of disclosure primary attention herein has been directed toward a system employing RF power as the source of energy delivered to the remote station, and such is currently the preferred approach, it will be appreciated that alternate sources of power may be employed. A light beam, for example, with suitable means for receiving the light on the remote station and converting it to responsive electrical output, such as an appropriate DC voltage may be employed. The converter devices, such as CMOS or TTL, could provide voltages at desired levels and currents on the order of milliamps to power the device.

Whereas particular embodiments of the invention have been described above for purposes of illustration, it will be appreciated by those skilled in the art that numerous variations of the details may be made without departing from the invention as described in the appended claims.

What is claimed is:

1. Apparatus for remote interaction with an object of interest comprising
   a remote station for obtaining information from said object of interest,
   a base station for transmitting energy in space to and communicating with said remote station,
   said base station having means for transmitting said energy as RF power,
   said remote station having conversion means for energizing said remote station response to receipt of said transmitted energy,
   said remote station not having a power storage device for energizing said remote station after termination of base station energy transmission to said remote station,
   first antenna means operatively associated with said base station for transmitting signals to and receiving signals from said remote station, and second antenna means operatively associated with said remote station for receiving signals from said first antenna means and transmitting signals to said first antenna means.

2. The apparatus of claim 1 including
a power supply for energizing said base station.

3. The apparatus of claim 2 including
first controller means for controlling operation of said base station.

4. The apparatus of claim 3 including
said first controller means has microprocessor means.

5. The apparatus of claim 1 including
said remote station having means for converting said transmitted energy into DC power for immediately energizing said remote station.

6. The apparatus of claim 5 including
said remote station having second controller means for processing information received from said base station and for transmitting information in space to said base station.

7. Apparatus for remote interaction with an object of interest comprising
a remote station for obtaining information from said object of interest,
a base station for transmitting energy in space to and communicating with said remote station,
said remote station having conversion means for energizing said remote station responsive to receipt of said transmitted energy,
said remote station not having a power storage device for energizing said remote station after termination of base station energy transmission to said remote station,
said base station having means for transmitting said energy as RF power,
a power supply for energizing said base station,
first controller means for controlling operation of said base station,
said first controller means has microprocessor means,
first antenna means operatively associated with said base station for transmitting signals to and receiving signals from said remote station,
second antenna means operatively associated with said remote station for receiving signals from said first antenna means and transmitting signals to said first antenna means,
said remote station having means for converting said transmitted energy into DC power for immediately energizing said remote station,
said remote station having second controller means for processing information in space received from said base station and for transmitting information to said base station, and
said second controller means having means for receiving information from sensor means monitoring said object of interest.

8. The apparatus of claim 7 including
said remote station not having a power storage device physically secured thereto.

9. The apparatus of claim 7 including
said base station and said remote station having no wired connection therebetween.

10. The apparatus of claim 7 including
said remote station having at least one transponder for receiving the value of a parameter measured by said sensor means and transmitting the same to said base station.

11. The apparatus of claim 10 including
said sensor means having a plurality of sensors, and
a said transponder operatively associated with each said sensor.

12. The apparatus of claim 11 including
said base station having means for sequentially interrogating said transponders.

13. The apparatus of claim 12 including
said base station transmitting both power signals and data signals to said remote station.

14. The apparatus of claim 10 including
said remote station having maximum dimensions of about 5 inches by 2 inches by 1 inch.

15. The apparatus of claim 11 including
said sensors being EKG sensors.

16. Apparatus for remote interaction with an object of interest comprising
a remote station for obtaining information from said object of interest,
a base station for transmitting energy in space to and communicating with said remote station,
said remote station having conversion means for energizing said remote station responsive to receipt of said transmitted energy,
said remote station not having a power storage device for energizing said remote station after termination of base station energy transmission to said remote station,
said base station having means for transmitting said energy as RF power,
a power supply for energizing said base station,
first controller means for controlling operation of said base station,
said first controller means has microprocessor means,
first antenna means operatively associated with said base station for transmitting signals to and receiving signals from said remote station,
second antenna means operatively associated with said remote station for receiving signals from said first antenna means and transmitting signals to said first antenna means,
said remote station having means for converting said transmitted energy into DC power for immediately energizing said remote station,
said remote station having second controller means for processing information in space received from said base station and for transmitting information to said base station, and
said remote station being structured to be operatively associated with said object of interest which is a patient.

17. The apparatus of claim 16 including
said sensor means having apparatus to monitor a body condition or body function of said patient.

18. Apparatus for remote interaction with an object of interest comprising
a remote station for obtaining information from said object of interest,
a base station for transmitting energy in space to and communicating with said remote station,
said remote station having conversion means for energizing said remote station responsive to receipt of said transmitted energy,
said remote station not having a power storage device for energizing said remote station after termination of base station energy transmission to said remote station, and said remote station being sealed within a resinous plastic material.

19. The apparatus of claim 18 including said remote station having converter means for converting said RF power into DC or AC power.

20. Apparatus for remote interaction with an object of interest comprising a remote station for obtaining information from said object of interest, a base station for transmitting energy in space to and communicating with said remote station, said remote station having conversion means for energizing said remote station responsive to receipt of said transmitted energy, said remote station not having a power storage device for energizing said remote station after termination of base station energy transmission to said remote station, said base station having means for transmitting said energy as RF power, and said remote station being sealed within a material selected from the group consisting of homopolymers, elastomers and silicon dioxide.

21. A method for remote interaction with an object of interest comprising providing a remote station and a base station operatively associated therewith, transmitting energy in space from said base station to said remote station, transmitting said energy as RF power, converting said energy received by said remote station into electrical power to energize said remote station, effecting said remote interaction without requiring such remote station to have a power storage device secured thereto for energizing said remote station after termination of said base station transmission and said energy conversion, and employing antenna means for communication of said RF power in space between said base station and said remote station.

22. A method for remote interaction with an object of interest comprising providing a remote station and a base station operatively associated therewith, transmitting energy in space from said base station to said remote station, converting said energy received by said remote station into electrical power to energize said remote station, effecting said remote interaction without requiring such remote station to have a power storage device secured thereto for energizing said remote station after termination of said base station transmission and said energy conversion, employing said method on an object of interest which is a patient, and monitoring said patient by sensor means and delivering information from said sensor means to at least one transponder on said remote station.

23. The method of claim 22 including energizing said base station by a power supply.

24. The method of claim 23 including converting said transmitted energy to DC power at said remote station.

25. The method of claim 23 including converting said transmitted energy into AC power at said remote station.

26. The method of claim 22 including employing said method to monitor a body condition or body function of said patient.

27. The method of claim 22 including positioning said remote station within 20 feet of said base station.

28. A method for remote interaction with an object of interest comprising providing a remote station and a base station operatively associated therewith, transmitting energy in space from said base station to said remote station converting said energy received by said remote station into electrical power to energize said remote station, effecting said remote interaction without requiring such remote station to have a power storage device secured thereto for energizing said remote station after termination of said base station transmission and said energy conversion, employing a plurality of transponders on said remote station, and sequentially interrogating said transponders to provide output therefrom to said base station.

29. The method of claim 28 including employing said method on an object of interest which is a patient.

30. The method of claim 28 including employing said transmitted energy as the sole source of power for said remote station.

31. The method of claim 28 including transmitting both power signals and data signals from said base station to said remote station.

32. The method of claim 31 including transmitting data signals in space from said remote station to said base station.

33. The method of claim 32 including employing a said remote station not having a power storage device.

34. The method of claim 33 including employing first microprocessor means to control operation of said base station.

35. The method of claim 34 including employing second microprocessor means to control said remote station.

36. The method of claim 28 including employing said method to confirm identification of an object of interest.

37. The method of claim 36 including employing said method in a security system.

38. A method for remote interaction with an object of interest comprising providing a remote station and a base station operatively associated therewith, transmitting energy in space from said base station to said remote station, converting said energy received by said remote station into electrical power to energize said remote station, effecting said remote interaction without requiring such remote station to have a power storage device secured thereto for energizing said remote station after termination of said base station transmission and said energy conversion, transmitting both power signals and data signals from said base station to said remote station, transmitting data signals in space from said remote station to said base station, employing a said remote station not having a power storage device, employing first microprocessor means to control operation of said base station, employing second microprocessor means to control said remote station, and employing sensor means which emit an electrical signal to said transponders.

39. The method of claim 38 including employing antenna means for communication between said base station and said remote station.

40. The method of claim 39 including creating a remote station having a maximum dimensions of about 5 inches by 2 inches by 1 inch.

* * * * *

UNITED STATES PATENT AND TRADEMARK OFFICE
CERTIFICATE OF CORRECTION

PATENT NO.    : 6,289,237 B1
DATED         : September 11, 2001
INVENTOR(S)   : Marlin H. Mickle et al.

It is certified that error appears in the above-identified patent and that said Letters Patent is hereby corrected as shown below:

Title page,
ABSTRACT,
Line 5, "conversion device" should read -- conversion means --.

Column 7,
Line 47, "(±15%)" should read -- (±5%) --.

Column 14,
Line 7, "creating" should read -- providing said --.
Line 7, delete "a" after "having".

Signed and Sealed this

Fifteenth Day of October, 2002

Attest:

Attesting Officer

JAMES E. ROGAN
*Director of the United States Patent and Trademark Office*